(12) United States Patent
Atsumi et al.

(10) Patent No.: US 9,750,936 B2
(45) Date of Patent: Sep. 5, 2017

(54) ELECTROSTIMULATOR AND CONTROL DEVICE OF SAME

(71) Applicant: Panasonic Intellectual Property Management Co., Ltd., Osaka (JP)

(72) Inventors: Sachiko Atsumi, Shiga (JP); Tadashi Arimura, Kyoto (JP); Hiroyuki Kaizo, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/150,299

(22) Filed: May 9, 2016

(65) Prior Publication Data

US 2016/0346539 A1    Dec. 1, 2016

(30) Foreign Application Priority Data

May 27, 2015    (JP) .................. 2015-107957

(51) Int. Cl.
| | | |
|---|---|---|
| A61N 1/00 | (2006.01) | |
| A61N 1/36 | (2006.01) | |
| A61N 1/04 | (2006.01) | |
| A61B 5/00 | (2006.01) | |
| A61B 5/11 | (2006.01) | |

(52) U.S. Cl.
CPC .......... *A61N 1/36003* (2013.01); *A61B 5/112* (2013.01); *A61B 5/6828* (2013.01); *A61N 1/0452* (2013.01); *A61N 1/36014* (2013.01); *A61B 2505/09* (2013.01)

(58) Field of Classification Search
CPC .......................... A61N 1/36003; A61N 1/0452
USPC ............................................................. 607/48
See application file for complete search history.

(56) References Cited

U.S. PATENT DOCUMENTS

| | | | |
|---|---|---|---|
| 6,456,885 B1 | 9/2002 | Shiba et al. | |
| 8,135,473 B2 * | 3/2012 | Miesel ................ | A61B 5/0205 |
| | | | 607/45 |

FOREIGN PATENT DOCUMENTS

JP        2000-279536        10/2000

* cited by examiner

*Primary Examiner* — Nadia A Mahmood
(74) *Attorney, Agent, or Firm* — McDermott Will & Emery LLP (57) ABSTRACT

A control device of an electrostimulator is used in the electrostimulator including an electrode, an angular velocity sensor, and a notifier. The control device includes a controller that controls electrostimulation which is output from the electrode and that counts the number of times of movements as the number of times of the reciprocating movements of the target site; and a storage that stores preset information. The storage stores a first threshold value and a second threshold value. The controller causes the notifier to display movement information including the number of times of the movements, based on a state in which an angular velocity reaches the second threshold value after reaching the first threshold value.

8 Claims, 4 Drawing Sheets

ELECTROSTIMULATOR AND CONTROL DEVICE OF SAME

BACKGROUND OF THE INVENTION

1. Field of the Invention

The present disclosure relates to an electrostimulator and a control device of the electrostimulator.

2. Description of the Related Art

There has been known an electrostimulator that outputs electrostimulation to an agonist muscle or an antagonist muscle. For example, an electrostimulator disclosed in Japanese Patent Unexamined Publication No. 2000-279536 applies electrostimulation to a leg during training of the leg, based on a change in an angle of a knee joint.

SUMMARY OF THE INVENTION

In a case where a user using the electrostimulator in the related art wants to know the number of times a movement is repeated, there is a need to count the number of times by oneself.

An object of the present disclosure is to provide an electrostimulator and a control device of the electrostimulator which contribute to provide the accurate number of movements for a user.

A control device of an electrostimulator according to an aspect of the present disclosure is used in the electrostimulator including an electrode that outputs electrostimulation to a target site of a human body which repeats reciprocating movements, a detector that outputs a signal in which motion of the target site is reflected, and a notifier that displays movement information as information related to the reciprocating movement. The control device includes: a controller that controls electrostimulation which is output from the electrode based on a detected value as a value obtained in response to the signal from the detector, and that counts the number of times of movements as the number of times of the reciprocating movements of the target site; and a storage that stores a first threshold value and a second threshold value which are compared with the detected value so as to count the number of times of the movements. The controller causes the notifier to displays the movement information including the number of times of the movements, based on a state in which the detected value reaches the first threshold value, and then, reaches the second threshold value.

A control device of an electrostimulator according to another aspect of the present disclosure is used in the electrostimulator including an electrode that outputs electrostimulation to a target site of a human body which repeats reciprocating movements and a detector that outputs a signal in which motion of the target site is reflected. The control device includes: a controller that controls electrostimulation which is output from the electrode based on a detected value as a value obtained in response to the signal from the detector, and that counts the number of times of movements as the number of times of the reciprocating movements of the target site; and a storage that stores a first threshold value and a second threshold value which are compared with the detected value so as to count the number of times of the movements. The controller increases a counter value that reflects the number of times of the movements, based on a state in which the detected value reaches the first threshold value, and then, reaches the second threshold value.

An electrostimulator according to still another aspect of the present disclosure includes: an electrode; a detector; a notifier that displays movement information as information related to reciprocating movement; and the control device described above.

The electrostimulator and the control device of the electrostimulator contribute to providing a user with the accurate number of times of movements.

DETAILED DESCRIPTION OF THE PREFERRED EMBODIMENTS

Example of Exemplary Embodiment of

A control device of an electrostimulator according to a first aspect of the present disclosure is used in the electrostimulator including an electrode that outputs electrostimulation to a target site of a human body which repeats reciprocating movements, a detector that outputs a signal in which motion of the target site is reflected, and a notifier that displays movement information as information related to the reciprocating movement. The control device includes: a controller that controls electrostimulation which is output from the electrode based on a detected value as a value obtained in response to the signal from the detector, and that counts the number of times of movements as the number of times of the reciprocating movements of the target site; and a storage that stores a first threshold value and a second threshold value which are compared with the detected value so as to count the number of times of the movements. The controller causes the notifier to display the movement information including the number of times of the movements, based on a state in which the detected value reaches the first threshold value, and then, reaches the second threshold value.

A user of the electrostimulator can know the number of times of the movements with reference to the movement information displayed from the notifier. In addition, according to the control device of the electrostimulator, the following effects are achieved, compared to another electrostimulator which counts the number of times of the movements, based on a relationship between the detected value and one threshold value.

Motion of a user may not be stable during training. For example, in a case where the user makes bending and extension movements, there is a difference between motion of the human body in ideal bending and extension movements and actual motion of the human body due to swaying of the upper body. In such a state in which the motion of the user is not stable in a case of using the other electrostimulator during training, there is a concern that a state in which the detected value exceeds the threshold value and the detected value becomes smaller than the threshold value will be repeated. In this case, the state, in which the detected value exceeds the threshold value, occurs a plurality of times in a state in which the user makes one bending and extension movement, and the other electrostimulator causes the notifier to display movement information including the number of times of the movements a plurality of times, based on the results. Therefore, accurate information related to the number of times of the movements is not provided to the user.

According to the control device of the electrostimulator, the movement information including the number of times of the movement is displayed from the notifier, based on the relationship between the detected value and the first threshold value and the second threshold value. Thus, even when the detected value changes due to an unstable motion of the user, there is less concern that the movement information is displayed from the notifier due to the change. Therefore, it is possible to provide accurate information related to the number of times of the movements to the user. Virtually the same effects as the effects achieved by the first aspect above are also achieved by the control device of the electrostimulator of a fourth aspect below.

According to a second aspect of the control device of the electrostimulator, in a case where one cycle of the movement of the target site is calculated based on the detected value, and the calculated one cycle is shorter than a predetermined one cycle, the controller maintains a state in which the number of times of the movements is displayed from the notifier.

Since, in the case of the unstable motion of the user, the target site vibrates in a short cycle, the one cycle becomes shorter. Therefore, the notifier is controlled as in the control device of the electrostimulator, and thereby there is less concern that inaccurate movement information will be provided to the user in the case of the unstable motion of the user. Virtually the same effects as the effects achieved by the second aspect above are also achieved by the control device of the electrostimulator of a fifth aspect below.

According to a third aspect of the control device of the electrostimulator, the controller calculates, based on the detected value, at least one of a first period as a period during which the target site moves from an initial position to a folded position during the reciprocating movement, or a second period as a period during which the target site moves from the folded position to the initial position during the reciprocating movement. The controller maintains a state in which the number of times of the movements is displayed from the notifier in a case where the calculated first period is shorter than a predetermined first period, or in a case where the calculated second period is shorter than a predetermined second period.

Since, in the case of the unstable motion of the user, the target site vibrates in a short cycle, at least one of the first cycle or the second cycle becomes shorter. Therefore, the notifier is controlled as in the control device of the electrostimulator, and thereby there is less concern that inaccurate movement information will be provided to the user in the case of the unstable motion of the user. Virtually the same effects as the effects achieved by the third aspect above are also achieved by the control device of the electrostimulator of a sixth aspect below.

A control device of an electrostimulator according to the fourth aspect of the present disclosure is used in the electrostimulator including an electrode that outputs electrostimulation to a target site of a human body which repeats reciprocating movements and a detector that outputs a signal in which motion of the target site is reflected. The control device includes: a controller that controls electrostimulation which is output from the electrode based on a detected value as a value obtained in response to the signal from the detector, and that counts the number of times of movements as the number of times of the reciprocating movements of the target site; and a storage that stores a first threshold value and a second threshold value which are compared with the detected value so as to count the number of times of the movements. The controller increases a counter value that reflects the number of times of the movements, based on a state in which the detected value reaches the first threshold value, and then, reaches the second threshold value.

According to a fifth aspect of the control device of the electrostimulator, in a case where the controller calculates one cycle of the movement of the target site based on the detected value, and the calculated one cycle is shorter than a predetermined one cycle, the controller does not increase the counter value.

According to a sixth aspect of the control device of the electrostimulator, the controller calculates, based on the detected value, at least one of a first period as a period during which the target site moves from an initial position to a folded position during the reciprocating movement, or a second period as a period during which the target site moves from the folded position to the initial position during the reciprocating movement. The controller does not increase the counter value in a case where the calculated first period is shorter than a predetermined first period, or in a case where the calculated second period is shorter than a predetermined second period.

An electrostimulator according to another aspect of the present disclosure includes: an electrode; a detector; a notifier that displays movement information as information related to reciprocating movement; and the control device of the first or the fourth aspect above. According to the electrostimulator, virtually the same effects as the effects achieved by the control device of the electrostimulator according to the first or the fourth aspect above are achieved.

Exemplary Embodiment 1

Figure 1:
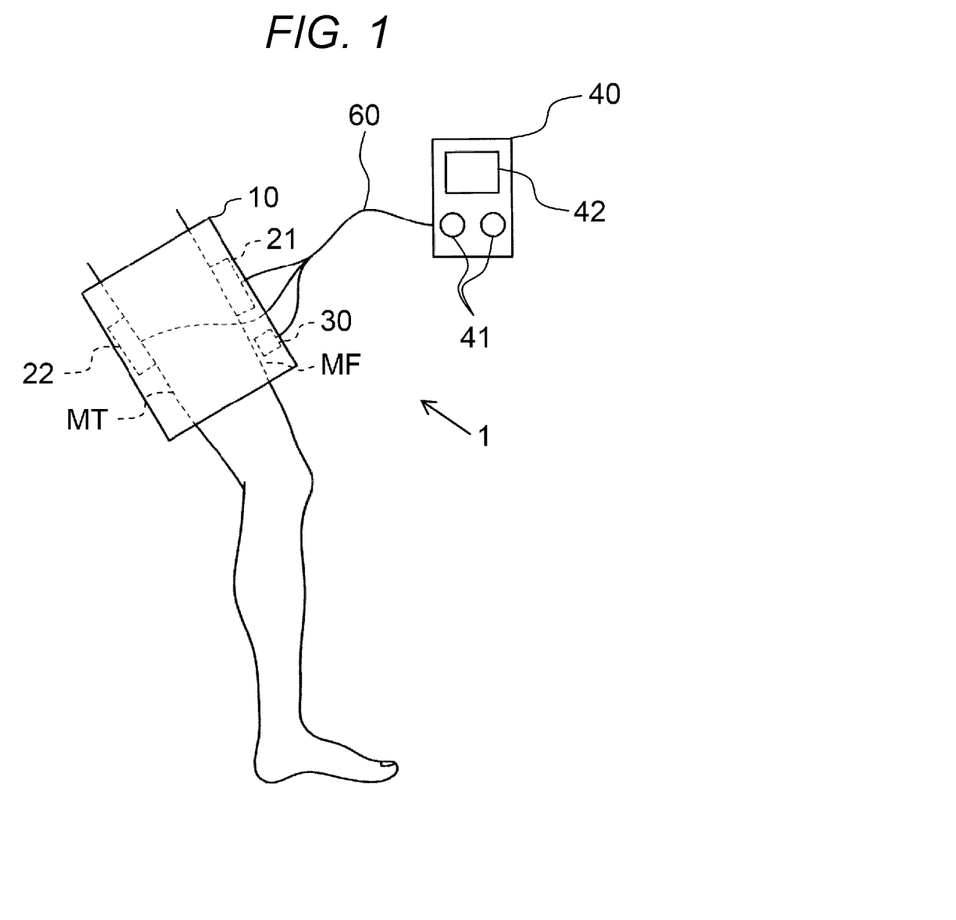
FIG. 1 is a schematic view illustrating an electrostimulator of Exemplary Embodiment 1.

FIG. 1 illustrates an example of a state of use of electrostimulator 1. Electrostimulator 1 includes a pair of supporters 10 put on a target site of a human body, which repeats reciprocating movements, first electrode 21 and second electrode 22 attached on an inner surface of each of supporters 10 so as to be exposed to the outside, and angular velocity sensor 30, as a detector, which is attached to each of supporters 10. In a case where electrostimulator 1 is used during bending and extension movements as an example of the reciprocating movement, supporter 10 is put on a thigh as the target site.

Supporter 10 for a right leg, which is put on a right thigh, and supporter 10 for a left leg, which is put on a left thigh, have a relationship of vertical symmetry with respect to the median plane of a human body. FIG. 1 illustrates supporter 10 for the left leg and supporter 10 for the right leg is omitted.

Each of electrodes 21 and 22 has a positive pole and a negative pole and outputs electrostimulation to muscles of a thigh which repeats bending and extension movements. First electrode 21 is disposed at a position facing quadriceps femoris MF, for example, in the state in which supporter 10 is put on the thigh. Second electrode 22 is disposed at a position facing biceps femoris MT, for example, in the state in which supporter 10 is put on the thigh.

When a knee joint is bent during the bending and extension movements, biceps femoris MT contracts as an agonist muscle and quadriceps femoris MF is extended as an antagonist muscle. On the other hand, when the knee joint is extended during the bending and extension movements, quadriceps femoris MF contracts as the agonist muscle and biceps femoris MT is extended as the antagonist muscle.

Angular velocity sensor 30 outputs a signal, for example, in which an angular velocity of a thigh rotating about a knee joint is reflected. The signal output from angular velocity sensor 30 indicates a positive value when the knee joint is bent and indicates a negative value when the knee joint is extended.

Electrostimulator 1 further includes controller 40 configured of a plurality of electric elements, and cable 60 that electrically connects electrodes 21, 22, angular velocity sensors 30, and controller 40. Controller 40 includes operator 41 for switching between ON and OFF of the power of electrostimulator 1, and notifier 42 which displays movement information as information related to the reciprocal movement. An example of notifier 42 is a display.

Figure 2:
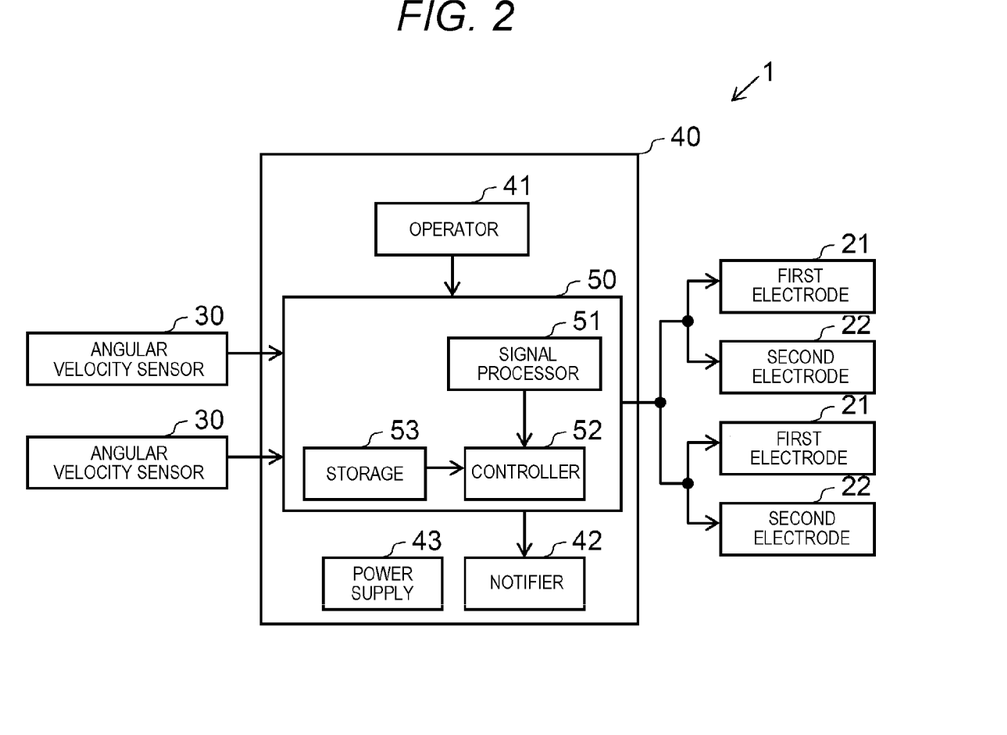
FIG. 2 is a block diagram of the electrostimulator in FIG. 1.

FIG. 2 illustrates a relation of electrical connection of electrostimulator 1. Controller 40 includes control device 50 that acquires a signal from each of angular velocity sensors 30, and power supply 43 that supplies power of a primary battery or a secondary battery to control device 50. Power supply 43 is electrically connected to operator 41 and notifier 42, in addition to control device 50.

Control device 50 includes signal processor 51 that performs a signal process on an input signal, controller 52 that controls electrostimulation which is output from each of electrodes 21 and 22 based on a detected result from each of angular velocity sensors 30, and storage 53 that stores preset information. Controller 52 controls electrodes 21 and 22 attached on supporter 10, for example, based on the detected results from angular velocity sensor 30 attached on one supporter 10 (refer to FIG. 1).

Signal processor 51 performs a signal process on the signal input from angular velocity sensor 30, thereby generating a sine wave signal. The signal processing includes removal of noise of a high frequency component, calculation of an average movement amount, frequency analysis, and the like. Signal processor 51 transmits an angular velocity as a detected value obtained from the generated sine wave signal to controller 52. Controller 52 controls electrostimulation which is output from each of electrodes 21 and 22, based on the angular velocity obtained from signal processor 51.

Storage 53 stores first threshold value T1 which is compared with the angular velocity for counting the number of times of the movements as the number of times of the reciprocating movements of the thigh, and second threshold value T2 which is compared with the angular velocity for counting the number of times of the movements and which is smaller than first threshold value T1. The sign of first threshold value T1 is opposite to the sign of second threshold value T2. In other words, first threshold value T1 exists in a positive region and second threshold value T2 exists in a negative region. In addition, first threshold value T1 and second threshold value T2 are used as threshold values which are compared with the angular velocity for controlling, for example, the outputting states from electrodes 21 and 22.

Controller 52 reads respective threshold values T1 and T2 from storage 53 and causes electrodes 21 and 22 to output electrostimulation, based on a state in which the angular velocity reaches one threshold value of first threshold value T1 or second threshold value T2, and then, reaches the other threshold value. Specifically, controller 52 determines that the angular velocity reaches second threshold value T2, and then, reaches first threshold value T1, thereby causing first electrode 21 to output electrostimulation. Therefore, the electrostimulation is applied to quadriceps femoris MF (refer to FIG. 1) as the antagonist muscle. Then, in a case where the electrostimulation is output from first electrode 21, controller 52 causes the outputting from first electrode 21 to be stopped, based on the state in which the angular velocity reaches second threshold value T2.

In comparison, controller 52 determines that the angular velocity reaches first threshold value T1, and then, reaches second threshold value T2, thereby causing second electrode 22 to output electrostimulation. Therefore, the electrostimulation is applied to biceps femoris MT (refer to FIG. 1) as the antagonist muscle. Then, in a case where the electrostimulation is output from second electrode 22, controller 52 causes the outputting from second electrode 22 to be stopped, based on a state in which the angular velocity reaches first threshold value T1. In this manner, controller 52 performs electrostimulation control that controls the electrostimulation which is output from electrodes 21 and 22, based on a relationship between the angular velocity and each of threshold values T1 and T2. Since the angular velocity is practically set to 0 when the bending and extension movements are started, controller 52 causes electrodes 21 and 22 corresponding to reached threshold values T1 and T2 to output the electrostimulation, based on a state in which the angular velocity reaches one threshold value of first threshold value T1 or second threshold value T2.

Controller 52 includes a counter that counts the number of times of the movements based on the angular velocity. Controller 52 reads respective threshold values T1 and T2 from storage 53, and increases, by 1, a value from the counter (hereinafter, referred to as a "counter value") which reflects the number of times of the movements, based on the state in which the angular velocity reaches second threshold value T2 after reaching first threshold value T1. Then, controller 52 performs counter control of outputting movement information including the number of times of the movements to notifier 42. According to the counter control, controller 52 outputs the movement information on notifier 42 whenever the counter value is increased, and the controller updates the movement information which is displayed from notifier 42. Controller 52 performs first control including, for example, electrostimulation control and counter control.

Figures 3A, 3B:
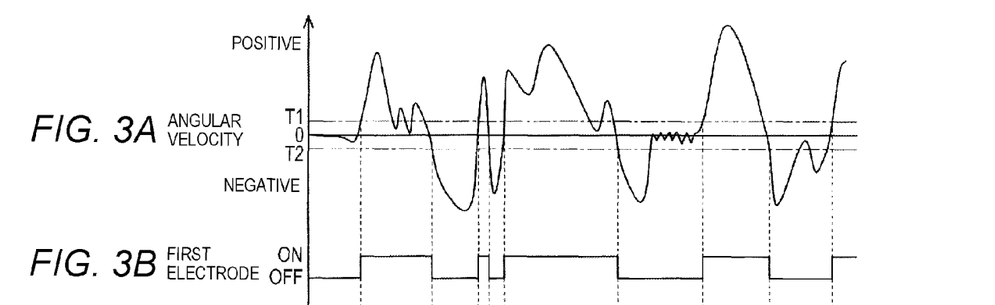
FIGS. 3A to 3D are time charts showing an example of first control.
Figure 3C:
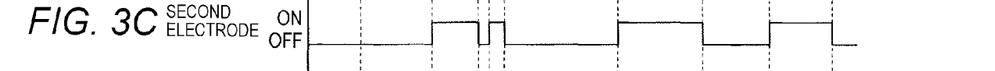
Figure 3D:
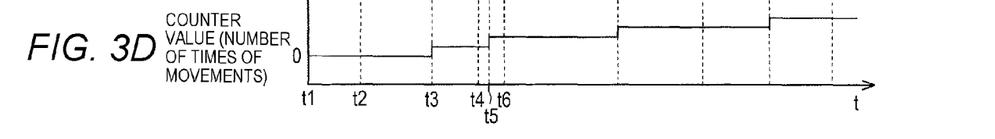

FIGS. 3A to 3D illustrate an example of a relationship between the angular velocity related to training, the outputting states from electrodes 21 and 22, and the counter value, when the first control is performed. A temporal change of the angular velocity is shown in FIG. 3A, the outputting state from first electrode 21 is shown in FIG. 3B, the outputting state from second electrode 22 is shown in FIG. 3C, and a change of the counter value (the number of times of the movements) is shown in FIG. 3D. In addition, since virtually the same detection results are obtained from respective angular velocity sensors 30 during the bending and extension movements, the angular velocity acquired from one angular velocity sensor 30 is omitted in FIG. 3A, and the outputting states from electrodes 21 and 22 corresponding to angular velocity sensor 30 are omitted in FIG. 3B.

At time point t1, a user using electrostimulator 1 operates operator 41 so as to switch the power of electrostimulator 1 from OFF to ON. The power of electrostimulator 1 is set to ON, and thereby each of angular velocity sensors 30 starts outputting, to controller 52, a signal, in which an angular velocity of a thigh is reflected. Then, the user starts, for example, training by cyclic bending and extension movements from a standing state.

At time point t2, controller 52 determines that the angular velocity changes from a value smaller than first threshold value T1 to a value equal to or greater than first threshold value T1. In other words, controller 52 determines that the angular velocity reaches first threshold value T1. Therefore, controller 52 causes first electrode 21 to output the electrostimulation, based on the state in which the angular velocity reaches first threshold value T1.

At time point t3, controller 52 determines that the angular velocity changes from the value equal to or greater than first threshold value T1 to a value equal to or smaller than second threshold value T2. In other words, controller 52 determines that the angular velocity reaches second threshold value T2 after reaching first threshold value T1. Therefore, controller 52 causes the outputting from first electrode 21 to be stopped and causes second electrode 22 to output the electrostimulation, based on the state in which the angular velocity reaches second threshold value T2.

In addition, at time point t3, controller 52 increases the counter value by 1, based on the state in which the angular velocity reaches second threshold value T2 after reaching first threshold value T1. Then, controller 52 causes notifier 42 to display the movement information including the number of times of the movements. At this time, notifier 42 displays the movement information indicating that the user makes one bending and extension movement.

At time point t4, controller 52 determines that the angular velocity changes from the value equal to or smaller than second threshold value T2 to a value equal to or greater than first threshold value T1. In other words, controller 52 determines that the angular velocity reaches first threshold value T1 after reaching second threshold value T2. Therefore, controller 52 causes the outputting from second electrode 22 to be stopped and causes first electrode 21 to output the electrostimulation, based on the state in which the angular velocity reaches first threshold value T1.

At time point t5, controller 52 determines that the angular velocity reaches second threshold value T2 after reaching first threshold value T1. Therefore, controller 52 causes the outputting from first electrode 21 to be stopped and causes second electrode 22 to output the electrostimulation, based on the state in which the angular velocity reaches second threshold value T2.

In addition, at time point t5, controller 52 increases the counter value by 1, based on the state in which the angular velocity reaches second threshold value T2 after reaching first threshold value T1. Then, controller 52 causes notifier 42 to display the movement information including the number of times of the movements. In other words, controller 52 updates the movement information which is displayed from notifier 42. At this time, notifier 42 displays the movement information indicating that the user makes two bending and extension movements.

At time point t6, controller 52 performs virtually the same process performed at time point t4. In this manner, controller 52 performs the first control, based on the relationship between the angular velocity and each of threshold values T1 and T2. In a case of continuing the bending and extension movements after time point t6, controller 52 repeatedly performs the same processes as the processes performed at time points t3 to t6.

Effects of electrostimulator 1 will be described with reference to FIGS. 1 and 2.

The user using electrostimulator 1 puts supporter 10 for the right leg on the right thigh and puts supporter 10 for the left leg on the left thigh. Here, each of supporters 10 is put on the thigh such that first electrode 21 is disposed at a position facing quadriceps femoris MF and second electrode 22 is disposed at a position facing biceps femoris MT. Then, the user attaches controller 40 to clothes or the like.

Before starting training, the user operates operator 41 so as to switch the power of electrostimulator 1 from OFF to ON. The power of electrostimulator 1 is set to ON, and thereby each of angular velocity sensor 30 starts outputting, to controller 52, the signal, in which an angular velocity of a thigh is reflected. Then, the user starts, for example, the bending and extension movements from a standing state.

Controller 52 performs the first control, based on the relationship between the angular velocity acquired from angular velocity sensor 30 and each or threshold values T1 and T2. Therefore, when the knee joint of the user is bent, the electrostimulation is output from first electrode 21 to quadriceps femoris MF as the antagonist muscle. In addition, when the user extends the knee joint, the electrostimulation is output from second electrode 22 to biceps femoris MT as the antagonist muscle. Therefore, training effects of the bending and extension movements are enhanced.

In addition, notifier 42 displays the movement information including the number of times of the movements as the user makes the bending and extension movements. Therefore, the user can know the number of times of the movements with reference to the movement information displayed from notifier 42.

According to control device 50 of Exemplary Embodiment 1, the following effects are further achieved.

(1) According to control device 50 of electrostimulator 1, the following effects are achieved, compared to another electrostimulator in which the number of times of the movements are counted based on the relationship between the angular velocity and one threshold value.

Motion of the user may not be stable during training. For example, in a case where the user makes bending and extension movements, there is a difference between motions of the human body in ideal bending and extension movements and actual motions of the human body due to swaying of the upper body. In such a state in which the motion of the user is not stable in a case of using the other electrostimulator during training, there is a concern that a state in which the angular velocity exceeds a threshold value and the angular velocity becomes smaller than the threshold value will be repeated. In this case, the state, in which the detected value exceeds the threshold value, occurs plurality of times in a state in which the user makes one bending and extension movement, and the other electrostimulator causes notifier 42 to display movement information including the number of times of the movements a plurality of times, based on the results. Therefore, accurate information related to the number of times of the movements is not provided to the user.

According to the control device 50, since the counter value is increased based on the relationship between the angular velocity and first threshold value T1 and second threshold value T2, and the movement information including the number of times of the movements is displayed from notifier 42. Thus, even when the detected value changes due to an unstable motion of the user, there is less concern that the movement information is displayed from notifier 42 due to the change. Therefore, it is possible to provide accurate information related to the number of times of the movements to the user.

(2) The bending and extension movements include a first period during which the thigh moves from an initial position to a folded position, and a second period during which the thigh moves from the folded position to the initial position. A typical example of the unstable motion of a user is a motion in which a speed of the motion of the thigh is changed within the first period or within the second period. According to control device 50, the sign of first threshold value T1 is opposite to the sign of second threshold value T2. Therefore, there is still less concern that the movement information including the number of times of the movements will be displayed from notifier 42, even when the angular velocity changes due to the unstable motion of the user.

(3) According to another electrostimulator that controls the outputting and the stopping of the electrostimulation which is applied to the thigh, based on the relationship between the angular velocity and one threshold value, in the state of unstable motion of the user, there is a concern that a state in which the angular velocity exceeds a threshold value and the angular velocity becomes smaller than the threshold value will be repeated in a short cycle. In this case, the outputting and the stopping of the electrostimulation applied to the thigh are repeated in a short cycle, and thus, the user is likely to be uncomfortable.

According to control device 50, the electrostimulation control is performed to control the electrostimulation output from electrodes 21 and 22, based on the relationship between the angular velocity and first threshold value T1 and second threshold value T2. Therefore, even when the angular velocity changes due to the unstable motion of the user and, for example, the angular velocity exceeds first threshold value T1, the electrostimulation is not output from second electrode 22 when the angular velocity does not reach second threshold value T2. The same is true of first electrode 21. Therefore, there is less concern that the outputting and the stopping of the electrostimulation will be repeated in the short cycle and the user is unlikely to be uncomfortable.

Exemplary Embodiment 2

Hereinafter, differences between control device 50 of electrostimulator 1 of Exemplary Embodiment 2 and control device 50 of electrostimulator 1 of Exemplary Embodiment 1 will be described, but control device 50 of electrostimulator 1 of Exemplary Embodiment 2 has virtually the same configuration as control device 50 of electrostimulator 1 of Exemplary Embodiment 1 except for the differences. In the following description of control device 50 of electrostimulator 1 of Exemplary Embodiment 2, the same reference signs are assigned to common configurations to control device 50 of electrostimulator 1 of Exemplary Embodiment 1, and a part of or entire description of the common configurations will be omitted.

Controller 52 further includes a timer (not illustrated) that measures a period of time. In a case where the outputting from first electrode 21 is stopped, controller 52 calculates, by using the timer, one cycle C of a movement of a thigh, as a period of time which elapses after the latest electrostimulation starts to be output from first electrode 21, based on the state in which the angular velocity reaches first threshold value T1 after reaching second threshold value T2. One cycle C corresponds to a period of elapsed time through the motion of the thigh from the initial position to the folded position, and further through the motion from the folded position to the initial position, for example, during the bending and extension movements.

In a case where calculated one cycle C is shorter than a predetermined one cycle set in advance, controller 52 does not increase the counter value. Controller 52 performs maintaining control of maintaining the number of times of the movements displayed from notifier 42. In other words, the movement information displayed from notifier 42 in the previous cycle is continuously displayed. The predetermined one cycle is stored in storage 53.

Controller 52 performs second control including, for example, the electrostimulation control, the counter control, and the maintaining control. According to the second control, it is determined that a condition for increasing the counter value is satisfied, for example, by the counter control, and it is determined that one cycle C is longer than the predetermined one cycle by the maintaining control, and thereby controller 52 increases the counter value by 1. In comparison, in a case where it is determined that one cycle C is shorter than the predetermined one cycle by the maintaining control even when it is determined that the condition for increasing the counter value is satisfied by the counter control, controller 52 does not increase the counter value.

Figure 4A:
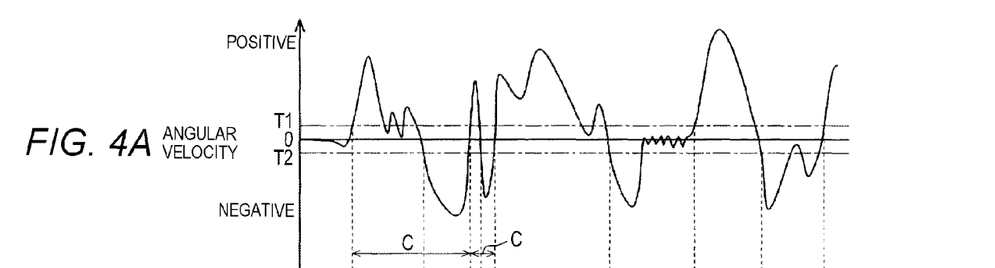
FIGS. 4A and 4B are time charts showing an example of second control.
Figure 4B:
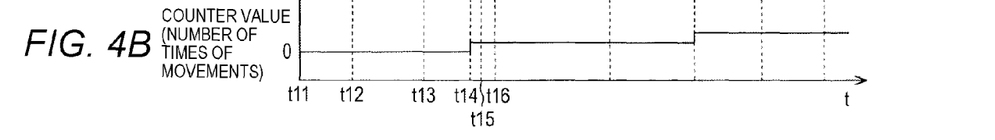

FIGS. 4A and 4B illustrate an example of a relationship between the angular velocity related to training and the counter value, when the second control is performed. A temporal change of the angular velocity is shown in FIG. 4A and a change of the counter value (the number of times of the movements) is shown in FIG. 4B. In addition, since the relationship between the angular velocity related to the training and the outputting states from electrodes 21 and 22, when the second control is performed, is virtually the same as the relationship between the angular velocity related to the training and the outputting states from electrodes 21 and 22, when the first control illustrated in FIGS. 3A to 3D is performed, a part of or entire description thereof is omitted.

At time point t11, a user using electrostimulator 1 operates operator 41 so as to switch the power of electrostimulator 1 from OFF to ON. The power of electrostimulator 1 is set to ON, and thereby each of angular velocity sensors 30 starts outputting, to controller 52, the signal, in which an angular velocity of a thigh is reflected. Then, the user starts, for example, training by cyclic bending and extension movements from a standing state.

At time point t12, controller 52 determines that the angular velocity reaches first threshold value T1. At time point t13, controller 52 determines that the angular velocity reaches second threshold value T2 after reaching first threshold value T1. Therefore, controller 52 determines that the condition for increasing the counter value is satisfied.

At time point t14, controller 52 determines that the angular velocity reaches first threshold value T1 after reaching second threshold value T2. In addition, controller 52 calculates one cycle C as a period of elapsed time from time point t12 to time point t14, and compares one cycle C with the predetermined one cycle set in advance.

In a case where controller 52 determines that one cycle C is longer than the predetermined one cycle, the controller increases the counter value based on the state in which the condition for increasing the counter value is satisfied. In comparison, in a case where controller 52 determines that one cycle C is shorter than the predetermined one cycle, the controller does not increase the counter value even when the condition for increasing the counter value is satisfied. Therefore, at time point t14, controller 52 determines that one cycle C is longer than the predetermined one cycle, thereby increasing the counter value by 1. At this time, notifier 42 displays the movement information indicating that the user makes one bending and extension movement.

At time point t15, controller 52 determines that the angular velocity reaches second threshold value T2 after reaching first threshold value T1. Therefore, controller 52 determines that the condition for increasing the counter value is satisfied.

At time point t16, controller 52 determines that the angular velocity reaches first threshold value T1 after reaching second threshold value T2. In addition, controller 52 calculates one cycle C in the same manner as in the process performed at time point t14, and compares one cycle C with the predetermined one cycle. At time point t16, controller 52 determines that one cycle C is shorter than the predetermined one cycle, thereby not increasing the counter value. Therefore, at time point t14, controller 52 maintains the movement information displayed from notifier 42. In other words, notifier 42 continuously displays the movement information indicating that the user makes one bending and extension movement.

In this manner, controller 52 performs the second control, based on the relationship between the angular velocity and each of threshold values T1 and T2, and the relationship between one cycle C and the predetermined one cycle. In a case of continuing the bending and extension movements after time point t16, controller 52 repeatedly performs the same processes as the processes performed at time points t13 to t16.

In addition, when the user ends the bending and extension movement, the angular velocity may not reach first threshold value T1 after reaching second threshold value T2. In this case, the latest bending and extension movement is not reflected in the number of times of the movements. Therefore, in a case where the angular velocity does not reach first threshold value T1 when a predetermined period of time elapses after the condition for increasing the counter value is satisfied, controller 52 increases the counter value. Therefore, accurate information related to the number of times of the movements is provided to the user.

According to control device 50 of Exemplary Embodiment 2, in addition to the effects of (1) to (3) achieved by Exemplary Embodiment 1, the following effect is further achieved.

(4) Since, in the case of the unstable motion of the user, the thigh vibrates in a short cycle, for example, one cycle C become shorter. Based on this state, control device 50 performs maintaining control of maintaining the number of times of the movements displayed from notifier 42, without increasing the counter value in the case where one cycle C is shorter than the predetermined one cycle. Therefore, in the case of the unstable motion of the user, there is less concern that inaccurate movement information will be provided to the user.

Exemplary Embodiment 3

Hereinafter, differences between control device 50 of electrostimulator 1 of Exemplary Embodiment 3 and control device 50 of electrostimulator 1 of Exemplary Embodiment 1 will be described, but control device 50 of electrostimulator 1 of Exemplary Embodiment 3 has virtually the same configuration as control device 50 of electrostimulator 1 of Exemplary Embodiment 1 except for the differences. In the following description of control device 50 of electrostimulator 1 of Exemplary Embodiment 3, the same reference signs are assigned to common configurations to control device 50 of electrostimulator 1 of Exemplary Embodiment 1, and a part of or entire description of the common configurations will be omitted.

Controller 52 further includes a timer (not illustrated) that measures a period of time. Controller 52 calculates first period TH1 as a period during which the thigh moves from the initial position to the folded position in the bending and extension movements. First period TH1 corresponds to, for example, a period of time in which the angular velocity changes from a value equal to or greater than first threshold value T1 to a value equal to or smaller than second threshold value T2, after the angular velocity changes from a value smaller than first threshold value T1 to a value equal to or greater than first threshold value T1, and means a period in which the knee joint is virtually bent. Therefore, in a case where the outputting from second electrode 22 is stopped, controller 52 calculates, by using the timer, first period TH1 as a period of elapsed time after the outputting from second electrode 22 is stopped, based on the state in which the angular velocity reaches second threshold value T2 after reaching first threshold value T1.

In addition, controller 52 calculates second period TH2 as a period during which the thigh moves from the folded position to the initial position in the reciprocating movement. Second period TH2 corresponds to, for example, a period of time in which the angular velocity changes from a value equal to or smaller than second threshold value T2 to a value equal to or greater than first threshold value T1, after the angular velocity changes from a value equal to or greater than first threshold value T1 to a value equal to or smaller than second threshold value T2, and means a period in which the knee joint is virtually extended. Therefore, in a case where the outputting from first electrode 21 is stopped, controller 52 calculates, by using the timer, second period TH2 as a period of elapsed time after the outputting from first electrode 21 is stopped, based on the state in which the angular velocity reaches first threshold value T1 after reaching second threshold value T2.

In a case where calculated first period TH1 is shorter than a predetermined first period set in advance, or in a case where calculated second period TH2 is shorter than a predetermined second period set in advance, controller 52 does not increase the counter value. Then, controller 52 performs another type of maintaining control of maintaining the number of times of the movements displayed from notifier 42. In other words, the movement information displayed from notifier 42 in the previous cycle is continuously displayed. The predetermined first period and the predetermined second period are stored in storage 53.

Controller 52 performs third control including, for example, the electrostimulation control, the counter control, and the other type of maintaining control. According to the third control, it is determined that a first condition as a condition for increasing the counter value is satisfied, for example, by the counter control, and it is determined that a second condition as a condition for not increasing the counter value is not satisfied by the other type of maintaining control, and thereby controller 52 increases the counter value by 1. In comparison, even when it is determined that the first condition is satisfied by the counter control, controller 52 does not increase the counter value in a case where it is determined that the second condition is satisfied by the other type of maintaining control.

Figure 5A:
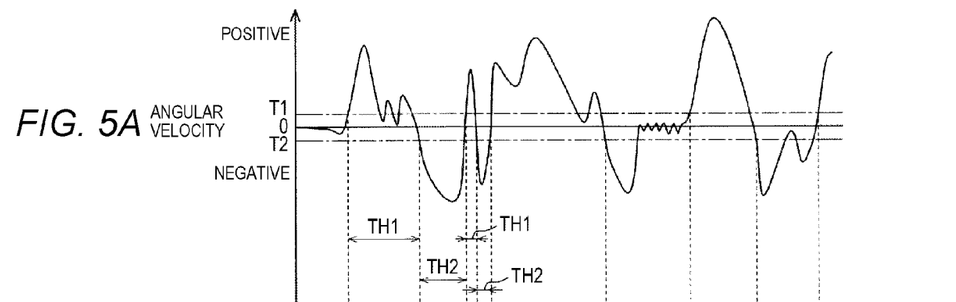
FIGS. 5A and 5B are time charts showing an example of third control.
Figure 5B:
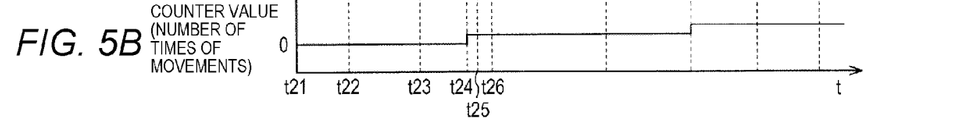

FIGS. 5A and 5B illustrate an example of a relationship between the angular velocity related to training and the counter value, when the third control is performed. A temporal change of the angular velocity is shown in FIG. 5A and a change of the counter value (the number of times of the movements) is shown in FIG. 5B. In addition, since the relationship between the angular velocity related to the training and the outputting states from electrodes 21 and 22, when the third control is performed, is virtually the same as the relationship between the angular velocity related to the training and the outputting states from electrodes 21 and 22, when the first control illustrated in FIGS. 3A to 3D is performed, a part of or entire description thereof is omitted.

At time point t21, the user using electrostimulator 1 operates operator 41 so as to switch the power of electrostimulator 1 from OFF to ON. The power of electrostimulator 1 is set to ON, and thereby each of angular velocity sensors 30 starts outputting, to controller 52, the signal, in which the angular velocity of the thigh is reflected. Then, the user starts, for example, training by cyclic bending and extension movements from the standing state.

At time point t22, controller 52 determines that the angular velocity reaches first threshold value T1. At time point t23, controller 52 determines that the angular velocity reaches second threshold value T2 after reaching first threshold value T1. Therefore, controller 52 determines that the first condition is satisfied by the counter control. In addition, controller 52 calculates first period TH1 as a period of elapsed time from time point t22 to time point t23, and compares first period TH1 with the predetermined first period set in advance. At time point t23, controller 52 determines that first period TH1 is longer than the predetermined first period.

At time point t24, controller 52 determines that the angular velocity reaches first threshold value T1 after reaching second threshold value T2. In addition, controller 52 calculates second period TH2 as a period of elapsed time from time point t23 to time point t24, and compares second period TH2 with the predetermined second period set in advance. At time point t24, controller 52 determines that second period TH2 is longer than the predetermined second period.

At time point t23, in a case where controller 52 determines that first period TH1 is longer than the predetermined first period, and, at time point t24, determines that second period TH2 is longer than the predetermined second period, it is determined that the second condition is not satisfied by the maintaining control. Therefore, controller 52 increases the counter value by 1 based on the state in which the first condition is satisfied by the counter control. In comparison, in a case where controller 52 determines, at time point t23, that first period TH1 is shorter than the predetermined first period, or, at time point t24, determines that second period TH2 is shorter than the predetermined second period, it is determined that the second condition is satisfied by the maintaining control. Therefore, controller 52 does not increase the counter value even when the first condition is satisfied by the counter control.

At time point t23 and time point t24, controller 52 determines that the second condition is not satisfied by the maintaining control, thereby increasing the counter value by 1. Then, at time point t24, controller 52 causes notifier 42 to display the movement information including the number of times of the movements. At this time, notifier 42 displays the movement information indicating that the user makes one bending and extension movements.

At time point t25, controller 52 determines that the angular velocity reaches second threshold value T2 after reaching first threshold value T1. In addition, controller 52 calculates first period TH1 in the same manner as the process performed at time point t23, and compares first period TH1 with the predetermined first period. At time point t25, controller 52 determines that first period TH1 is shorter than the predetermined first period.

At time point t26, controller 52 determines that the angular velocity reaches first threshold value T1 after reaching second threshold value T2. In addition, controller 52 calculates second period TH2 in the same manner as the process performed at time point t24, and compares second period TH2 with the predetermined second period. At time point t26, controller 52 determines that second period TH2 is shorter than the predetermined second period.

At time point t25 and time point t26, controller 52 does not increase the counter value based on the state in which the second condition is satisfied by the maintaining control. At time point t24, controller 52 maintains the movement information displayed from notifier 42. Therefore, notifier 42 continuously displays the movement information indicating that the user makes one bending and extension movement. In the case where it is determined that first period TH1 is shorter than the predetermined first period, controller 52 may determine that the second condition is satisfied by the maintaining control, without comparing second period TH2 with the predetermined second period.

In this manner, controller 52 performs the third control, based on the relationship between the angular velocity and each of threshold values T1 and T2, the relationship between first period TH1 and the predetermined first period, and the relationship between second period TH2 and the predetermined second period. In a case of continuing the bending and extension movements after time point t26, controller 52 repeatedly performs the same processes as the processes performed at time points t23 to t26.

In addition, when the user ends the bending and extension movement, the angular velocity may not reach first threshold value T1 after reaching second threshold value T2. In this case, the latest bending and extension movement is not reflected in the number of times of the movements. Therefore, in a case where controller 52 determines that first period TH1 is longer than the predetermined first period, and the angular velocity does not reach first threshold value T1 when a predetermined period of time elapses after the first condition is satisfied by the counter control, controller 52 increases the counter value. Therefore, accurate information related to the number of times of the movements is provided to the user.

According to control device 50 of Exemplary Embodiment 3, in addition to the effects of (1) to (3) achieved by Exemplary Embodiment 1, the following effect is further achieved.

(5) Since, in the case of the unstable motion of the user, the thigh vibrates in a short cycle, for example, at least one of first period TH1 or second period TH2 becomes shorter. Based on this state, control device 50 performs the other type of maintaining control of maintaining the number of times of the movements displayed from notifier 42, without increasing the counter value in the case where first period TH1 is shorter than the predetermined first period, or in the case where second period TH2 is shorter than the second predetermined period. Therefore, in the case of the unstable motion of the user, there is less concern that inaccurate movement information will be provided to the user.

Exemplary Embodiment 4

Hereinafter, differences between control device 50 of electrostimulator 1 of Exemplary Embodiment 4 and control device 50 of electrostimulator 1 of Exemplary Embodiment 1 will be described, but control device 50 of electrostimulator 1 of Exemplary Embodiment 4 has virtually the same configuration as control device 50 of electrostimulator 1 of Exemplary Embodiment 1 except for the differences. In the following description of control device 50 of electrostimulator 1 of Exemplary Embodiment 4, the same reference signs are assigned to common configurations to control device 50 of electrostimulator 1 of Exemplary Embodiment 1, and a part of or entire description of the common configurations will be omitted.

Storage 53 stores reference threshold value K which is compared with the angular velocity for counting the number of times of the movements. Reference threshold value K exists virtually as a value of 0. First threshold value T1 and second threshold value T2 are not used as the threshold values which are compared with the angular velocity for counting the number of times of the movements.

Controller 52 further includes a timer (not illustrated) that measures a period of time. Controller 52 calculates positive time period TP as a period of time during which the angular velocity continuously exists in the positive region. Positive time period TP means, for example, a period of time in which the angular velocity changes from a value equal to or greater than reference threshold value K to a value smaller than reference threshold value K, after the angular velocity changes from a value smaller than reference threshold value K to a value equal to or greater than reference threshold value K. Therefore, controller 52 calculates, by using the timer, positive time period TP as a period of elapsed time after the angular velocity changes to a value equal to or greater than reference threshold value K, based on the state in which the angular velocity changes to a value smaller than reference threshold value K.

In addition, controller 52 calculates negative time period TM as a period of time during which the angular velocity continuously exists in the negative region. Negative time period TM means, for example, a period of time in which the angular velocity changes from a value smaller than reference threshold value K to a value equal to or greater than reference threshold value K, after the angular velocity changes from a value equal to or greater than reference threshold value K to a value smaller than reference threshold value K. Therefore, controller 52 calculates, by using the timer, negative time period TM as a period of elapsed time after the angular velocity changes to a value smaller than reference threshold value K, based on the state in which the angular velocity changes to a value equal to or greater than reference threshold value K.

Controller 52 increases the counter value by 1, based on a state in which the state in which calculated positive time period TP is longer than a preset first period of time, and the state in which calculated negative time period TM is longer than a preset second period of time are both satisfied. Then, controller 52 performs another type of counter control of causing notifier 42 to display the movement information including the number of times of the movements. According to the other type of counter control, controller 52 causes notifier 42 to display the movement information whenever increasing the counter value, and updates the movement information which is displayed from notifier 42. The first period of time and the second period of time are stored in storage 53. Controller 52 performs fourth control including, for example, the electrostimulation control and the other type of counter control.

Figure 6A:
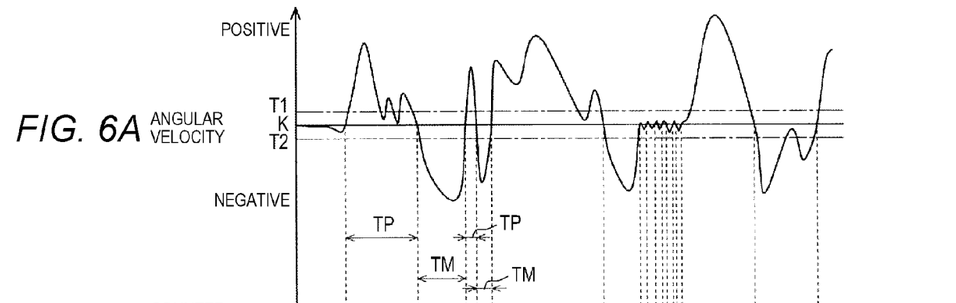
FIGS. 6A and 6B are time charts showing an example of fourth control.
Figure 6B:
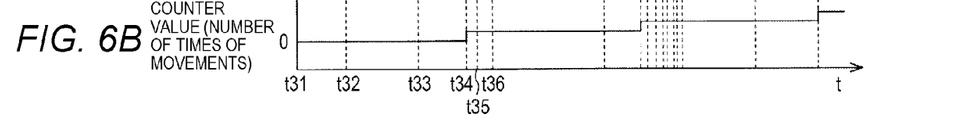

FIGS. 6A and 6B illustrate an example of a relationship between the angular velocity related to training and the counter value, when the fourth control is performed. A temporal change of the angular velocity is shown in FIG. 6A and a change of the counter value (the number of times of the movements) is shown in FIG. 6B. In addition, since the relationship between the angular velocity related to the training and the outputting states from electrodes 21 and 22, when the fourth control is performed, is virtually the same as the relationship between the angular velocity related to the training and the outputting states from electrodes 21 and 22, when the first control illustrated in FIGS. 3A to 3D is performed, a part of or entire description thereof is omitted.

At time point t31, the user using electrostimulator 1 operates operator 41 so as to switch the power of electrostimulator 1 from OFF to ON. The power of electrostimulator 1 is set to ON, and thereby each of angular velocity sensors 30 starts outputting, to controller 52, the signal, in which the angular velocity of the thigh is reflected. Then, the user starts, for example, training by cyclic bending and extension movements from the standing state.

At time point t32, controller 52 determines that the angular velocity changes from a value smaller than reference threshold value K to a value equal to or greater than reference threshold value K. At time point t33, controller 52 determines that the angular velocity changes from a value equal to or greater than reference threshold value K to a value smaller than reference threshold value K. In addition, controller 52 calculates time period TP, in which acceleration is within a positive range, as a period of elapsed time from time point t32 to time point t33, and compares positive time period TP with the preset first period of time. At time point t33, controller 52 determines that positive time period TP is longer than the first period of time.

At time point t34, controller 52 determines that the angular velocity changes from a value smaller than reference threshold value K to a value equal to or greater than reference threshold value K. In addition, controller 52 calculates time period TM, in which acceleration is within a negative range, as a period of elapsed time from time point t33 to time point t34, and compares negative time period TM with the preset second period of time. At time point t34, controller 52 determines that negative time period TM is longer than the second period of time.

Controller 52 increases the counter value by 1, based on a state in which the state in which positive time period TP is longer than the first period of time at time point t33, and the state in which negative time period TM is longer than the second period of time at time point t34 are both satisfied. In comparison, controller 52 does not increase the counter value, in a case where positive time period TP is shorter than the first period of time at time point t33, or in a case where negative time period TM is shorter than the second period of time at time point t34.

At time point t33 and time point t34, controller 52 increases the counter value by 1, based on a state in which the state in which positive time period TP is longer than the first period of time, and the state in which negative time period TM is longer than the second period of time are both satisfied. Then, at time point t34, controller 52 causes notifier 42 to display the movement information including the number of times of the movements. At this time, notifier 42 displays the movement information indicating that the user makes one bending and extension movement.

At time point t35, controller 52 determines that the angular velocity changes from a value equal to or greater than reference threshold value K to a value smaller than reference threshold value K. In addition, controller 52 calculates positive time period TP in the same manner as the process performed at time point t33, and compares positive time period TP with the first period of time. At time point t35, controller 52 determines that positive time period TP is shorter than the first period of time.

At time point t36, controller 52 determines that the angular velocity changes from a value smaller than reference threshold value K to a value equal to or greater than reference threshold value K. In addition, controller 52 calculates negative time period TM in the same manner as the process performed at time point t34, and compares negative time period TM with the second period of time. At time point t36, controller 52 determines that negative time period TM is shorter than the second period of time.

At time point t35 and time point t36, controller 52 determines that positive time period TP is shorter than the first period of time, or determines that negative time period TM is shorter than the second period of time, thereby not increasing the counter value. Then, at time point t34, controller 52 maintains the movement information displayed from notifier 42. Therefore, notifier 42 continuously displays the movement information indicating that the user makes one bending and extension movement. In the case where it is determined that positive time period TP is shorter than the first period of time, controller 52 may not compare negative time period TM with the second period of time.

In this manner, controller 52 performs the fourth control, based on the relationship between the angular velocity and each of threshold values T1 and T2, the relationship between positive time period TP and the first period of time, and the relationship between negative time period TM and the second period of time. In a case of continuing the bending and extension movements after time point t36, controller 52 repeatedly performs the same processes as the processes performed at time points t33 to t36.

According to control device 50 of Exemplary Embodiment 4, in addition to the effect of (3) achieved by Exemplary Embodiment 1, the following effect is further achieved.

(6) Since, in the case of the unstable motion of the user, the thigh vibrates in a short cycle, for example, positive time period TP and negative time period TM become shorter. Based on this state, control device 50 increases the counter value by 1, based on a state in which the state in which positive time period TP is longer than the first period of time, and the state in which negative time period TM is longer than the second period of time are both satisfied. The control device performs the other type of counter control of causing notifier 42 to display the movement information including the number of times of the movements. Therefore, in the case of the unstable motion of the user, there is less concern that inaccurate movement information will be provided to the user.

Modification Example

The exemplary embodiments are described above as examples of exemplary embodiments of the electrostimulator and the control device of the electrostimulator according to the present disclosure, and the exemplary embodiments thereof are not limited to the exemplary embodiments described above. The electrostimulator and the control device of the electrostimulator according to the present disclosure can be realized, for example, as the following modification examples of the exemplary embodiments described above, and as an exemplary embodiment achieved by combining at least two modification examples which are not incompatible, as well as the exemplary embodiment described above.

Controller 52 of a modification example of Exemplary Embodiment 2 performs another type of second control further including another type of maintaining control, in addition to the electrostimulation control, the counter control, and the maintaining control.

Controller 52 of another modification example of Exemplary Embodiment 2 calculates, by using the timer, one cycle of the movement of the thigh, as a period of time elapsed after the latest electrostimulation starts to be output from second electrode 22, based on the state in which the angular velocity reaches second threshold value T2 after reaching first threshold value T1, for example, in the case where the outputting from second electrode 22 is stopped. The one cycle corresponds to a period of elapsed time through the motion of the thigh from the folded position to the initial position, and further through the motion from the initial position to the folded position, for example, during the bending and extension movements. In the case where the calculated one cycle is shorter than the predetermined one cycle set in advance, controller 52 does not increase the counter value. Controller 52 performs maintaining control of maintaining the number of times of the movements displayed from notifier 42.

Controller 52 of still another modification example of Exemplary Embodiment 2 performs another type of second control, instead of the second control. According to the other type of second control, it is determined that the condition for increasing the counter value is satisfied by the counter control, and thereby controller 52 increases the counter value by 1. Also, controller 52 determines that one cycle C is longer than the predetermined one cycle by the maintaining control, thereby causing notifier 42 to display the movement information including the number of times of the movements. In comparison, controller 52 determines that one cycle C is shorter than the predetermined one cycle by the maintaining control, thereby decreasing the counter value by 1, and maintaining the number of times of the movements which is displayed from notifier 42. Further, the same modification is performed also in Exemplary Embodiment 3 and Exemplary Embodiment 4.

Controller 52 of another modification example performs still another type of second control, instead of the second control. According to still the other type of second control, in the case where controller 52 determines that one cycle C is longer than the predetermined one cycle by the maintaining control, then, the condition for increasing the counter value is satisfied by the counter control, thereby increasing the counter value by 1. Also, controller 52 causes notifier 42 to display the movement information including the number of times of the movements. In comparison, controller 52 does not increase the counter value, in the case where it is determined that one cycle C is shorter than the predetermined one cycle by the maintaining control, then, even when the condition for increasing the counter value is satisfied by the counter control. Further, the same modification is performed also in Exemplary Embodiment 3 and Exemplary Embodiment 4.

Controller 52 of a modification example of Exemplary Embodiment 3 does not calculate second period TH2. In the modification example, controller 52 determines that first period TH1 is shorter than the predetermined first period set in advance, thereby performing still another type of maintaining control of maintaining the number of times of the movements which is displayed from notifier 42 without increasing the counter value.

Controller 52 of another modification example of Exemplary Embodiment 3 does not calculate first period TH1. In the modification example, controller 52 determines that second period TH2 is shorter than the predetermined second period set in advance, thereby performing still another type of maintaining control of maintaining the number of times of the movements which is displayed from notifier 42 without increasing the counter value.

Controller 52 of a modification example of Exemplary Embodiment 4 performs another type of fourth control further including at least one of the maintaining control or another type of maintaining control, in addition to the electrostimulation control and another type of counter control.

Controller 52 of another modification example of Exemplary Embodiment 4 increases the counter value by 1, based on the state in which one of the state in which positive time period TP is longer than the first period of time, or the state in which negative time period TM is longer than the second period of time is satisfied. The controller causes notifier 42 to display the movement information including the number of times of the movements. According to the modification example, controller 52 does not increase the counter value, only in a case where the state in which positive time period TP is shorter than the first period of time, and the state in which negative time period TM is shorter than the second period of time are both satisfied.

Controller 52 of still another modification example of Exemplary Embodiment 4 increases the counter value by 1, based on the state in which the state, in which one cycle of the movement of the thigh is longer than the predetermined one cycle, is satisfied. Instead of or in addition of the other type of counter control, the controller performs still another type of counter control of causing notifier 42 to display the movement information including the number of times of the movements. The one cycle means a sum of, for example, positive time period TP and negative time period TM. The predetermined one cycle is longer than a sum of the first period of time and the second period of time.

The relationship between first threshold value T1 and second threshold value T2 which are stored in storage 53 of a modification example is an option. According to an example, first threshold value T1 exists in the negative region and second threshold value T2 exists in the positive region.

Whether or not the sign of first threshold value T1 is opposite to the sign of second threshold value T2 is an option. According to an example, first threshold value T1 exists in the positive region and second threshold value T2 is virtually a value of 0.

Controller 52 of a modification example performs another type of electrostimulation control of controlling the outputting states of electrodes 21 and 22, regardless of the relationship between the angular velocity and each of threshold values T1 and T2. According to the other type of electrostimulation control, the outputting states of electrodes 21 and 22 are controlled based on the relationship between the angular velocity and one threshold value.

Power supply 43 of a modification example supplies, to control device 50, power obtained from a commercial power supply, instead of the primary battery or the secondary battery.

Notifier 42 of a modification example outputs information in voice.

Electrostimulator 1 of a modification example includes a touch panel display having a function of operator 41 and a function of notifier 42, instead of operator 41 and notifier 42.

Electrostimulator 1 of a modification example may also omit notifier 42 from controller 40.

Electrostimulator 1 of a modification example includes an acceleration sensor as another detector, instead of angular velocity sensor 30.

Electrostimulator 1 of a modification example can have a configuration in which angular velocity sensor 30 attached to one supporter 10 is omitted. According to the modification example, the electrostimulation which is output from each of electrodes 21 and 22 is controlled, based on the detection result from one angular velocity sensor 30.

Whether or not controller 52 causes each of electrodes 21 and 22 to output the electrostimulation to the antagonist muscle is an option. According to an example, controller 52 causes each of electrodes 21 and 22 to output the electrostimulation to the agonist muscle. In this case, since biceps femoris MT contracts as the agonist muscle when the knee joint is bent, controller 52 causes second electrode 22 to output the electrostimulation. In addition, since quadriceps femoris MF contracts as the agonist muscle when the knee joint is extended, controller 52 causes first electrode 21 to output the electrostimulation.

Whether or not electrostimulator 1 is used during the bending and extension movements is an option. In a case where electrostimulator 1 is used during arm curl as another example of the reciprocating movement, supporter 10 is put on an arm. In this case, electrodes 21 and 22 are disposed at positions facing biceps femoris and triceps femoris in the state in which supporter 10 is put on the arm.

Appendixes According to Solution to Problem

A control device of an electrostimulator according to another first aspect of present disclosure is used in the electrostimulator including an electrode that outputs electrostimulation to a target site of a human body which repeats reciprocating movements, a detector that outputs a signal in which motion of the target site is reflected, and a notifier that displays movement information as information related to the reciprocating movement. The control device includes: a controller that controls electrostimulation which is output from the electrode based on a detected value as a value obtained in response to the signal from the detector, and that counts the number of times of movements as the number of times of the reciprocating movements of the target site. The controller causes the notifier to display the movement information including the number of times of the movements, based on a state in which at least one of a state in which a period of time, during which the detected value continuously exists in a positive region, is longer than a first period of time, or a state in which a period of time, during which the detected value continuously exists in a negative region, is longer than a second period of time, is satisfied.

A control device of an electrostimulator according to another second aspect of present disclosure is used in the electrostimulator including an electrode that outputs electrostimulation to a target site of a human body which repeats reciprocating movements, a detector that outputs a signal in which motion of the target site is reflected, and a notifier that displays movement information as information related to the reciprocating movement. The control device includes: a controller that controls electrostimulation which is output from the electrode based on a detected value as a value obtained in response to the signal from the detector, and that counts the number of times of movements as the number of times of the reciprocating movements of the target site. The controller calculates one cycle of the movement of the target site based on the detected value, and causes the notifier to display the movement information including the number of times of the movements, based on a state in which the calculated one cycle is shorter than the predetermined one cycle.

The electrostimulator and the control device of the electrostimulator can be used in various types of electrostimulator including household or business one.

What is claimed is:

1. A control device of an electrostimulator, which is used in the electrostimulator including an electrode that outputs electrostimulation to a target site of a human body which repeats reciprocating movements, a detector that outputs a signal in which motion of the target site is reflected, and a notifier that displays movement information as information related to the reciprocating movement, the control device comprising:

a controller that controls electrostimulation which is output from the electrode based on a detected value as a value obtained in response to the signal from the detector, and that counts the number of times of movements as the number of times of the reciprocating movements of the target site; and a storage that stores a first threshold value and a second threshold value which are compared with the detected value so as to count the number of times of the movements, wherein:

the controller causes the notifier to display the movement information including the number of times of the movements, based on a state in which the detected value reaches the first threshold value, and then, reaches the second threshold value, and in a case where one cycle of the movement of the target site is calculated based on the detected value, and the calculated one cycle is shorter than a predetermined one cycle, the controller maintains a state in which the number of times of the movements is displayed from the notifier.

2. A control device of an electrostimulator, which is used in the electrostimulator including an electrode that outputs electrostimulation to a target site of a human body which repeats reciprocating movements, a detector that outputs a signal in which motion of the target site is reflected, and a notifier that displays movement information as information related to the reciprocating movement, the control device comprising:

a controller that controls electrostimulation which is output from the electrode based on a detected value as a value obtained in response to the signal from the detector, and that counts the number of times of movements as the number of times of the reciprocating movements of the target site; and a storage that stores a first threshold value and a second threshold value which are compared with the detected value so as to count the number of times of the movements, wherein:

the controller causes the notifier to display the movement information including the number of times of the movements, based on a state in which the detected value reaches the first threshold value, and then, reaches the second threshold value, and the controller calculates, based on the detected value, at least one of a first period as a period during which the target site moves from an initial position to a folded position during the reciprocating movement, or a second period as a period during which the target site moves from the folded position to the initial position during the reciprocating movement, and maintains a state in which the number of times of the movements is displayed from the notifier in a case where the calculated first period is shorter than a predetermined first period, or in a case where the calculated second period is shorter than a predetermined second period.

3. A control device of an electrostimulator, which is used in the electrostimulator including an electrode that outputs electrostimulation to a target site of a human body which repeats reciprocating movements and a detector that outputs a signal in which motion of the target site is reflected, the control device comprising:

a controller that controls electrostimulation which is output from the electrode based on a detected value as a value obtained in response to the signal from the detector, and that counts the number of times of movements as the number of times of the reciprocating movements of the target site; and a storage that stores a first threshold value and a second threshold value which are compared with the detected value so as to count the number of times of the movements, wherein:

the controller increases a counter value that reflects the number of times of the movements, based on a state in which the detected value reaches the first threshold value, and then, reaches the second threshold value, and in a case where the controller calculates one cycle of the movement of the target site based on the detected value, and the calculated one cycle is shorter than a predetermined one cycle, the controller does not increase the counter value.

4. A control device of an electrostimulator, which is used in the electrostimulator including an electrode that outputs electrostimulation to a target site of a human body which repeats reciprocating movements and a detector that outputs a signal in which motion of the target site is reflected, the control device comprising:

a controller that controls electrostimulation which is output from the electrode based on a detected value as a value obtained in response to the signal from the detector, and that counts the number of times of movements as the number of times of the reciprocating movements of the target site; and a storage that stores a first threshold value and a second threshold value which are compared with the detected value so as to count the number of times of the movements, wherein:

the controller increases a counter value that reflects the number of times of the movements, based on a state in which the detected value reaches the first threshold value, and then, reaches the second threshold value, and the controller calculates, based on the detected value, at least one of a first period as a period during which the target site moves from an initial position to a folded position during the reciprocating movement, or a second period as a period during which the target site moves from the folded position to the initial position during the reciprocating movement, and does not increase the counter value in a case where the calculated first period is shorter than a predetermined first period, or in a case where the calculated second period is shorter than a predetermined second period.

5. An electrostimulator comprising:
the electrode;
the detector;
the notifier that displays movement information as information related to reciprocating movement; and
the control device of claim 1.

6. An electrostimulator comprising:
the electrode;
the detector;
the notifier that displays movement information as information related to reciprocating movement; and
the control device of claim 3.

7. An electrostimulator comprising:
the electrode;
the detector;
the notifier that displays movement information as information related to reciprocating movement; and
the control device of claim 2.

8. An electrostimulator comprising: the electrode; the detector;

the notifier that displays movement information as information related to reciprocating movement; and the control device of claim 4.

\* \* \* \* \*